United States Patent
Miyano

(10) Patent No.: US 6,852,079 B2
(45) Date of Patent: Feb. 8, 2005

(54) LIGHT GUIDE AND ENDOSCOPE

(75) Inventor: Hitoshi Miyano, Saitama (JP)

(73) Assignee: Fuji Photo Optical Co., Ltd., Saitama (JP)

( * ) Notice: Subject to any disclaimer, the term of this patent is extended or adjusted under 35 U.S.C. 154(b) by 183 days.

(21) Appl. No.: 10/023,624

(22) Filed: Dec. 18, 2001

(65) Prior Publication Data

US 2002/0076180 A1 Jun. 20, 2002

(30) Foreign Application Priority Data

Dec. 20, 2000 (JP) ........................................ 2000-386973

(51) Int. Cl.⁷ .............................................. A61B 1/06
(52) U.S. Cl. ..................................... 600/178; 600/180
(58) Field of Search ............................... 600/178–182; 362/574; 385/117, 119; 348/76

(56) References Cited

U.S. PATENT DOCUMENTS

| | | | | |
|---|---|---|---|---|
| 4,824,225 A | * | 4/1989 | Nishioka | ..................... 359/718 |
| 4,856,495 A | * | 8/1989 | Tohjoh et al. | ............... 600/175 |
| 4,952,040 A | * | 8/1990 | Igarashi | ....................... 359/708 |
| 5,485,316 A | * | 1/1996 | Mori et al. | .................. 359/708 |
| 5,587,839 A | * | 12/1996 | Miyano et al. | ............. 359/660 |
| 5,777,797 A | * | 7/1998 | Miyano | ....................... 359/660 |
| 5,827,172 A | * | 10/1998 | Takahashi et al. | ........... 600/176 |
| 5,980,454 A | * | 11/1999 | Broome | ....................... 600/176 |

\* cited by examiner

Primary Examiner—Roy D. Gibson
(74) Attorney, Agent, or Firm—Frommer Lawrence Haug LLP; Matthew K. Ryan, Esq.

(57) ABSTRACT

An object of the present invention is to make the light distribution by a light guide even. In the light guide, an amount of light emitted from the central region in the light emission end face is relatively small in comparison with an amount of light emitted from a peripheral region in the light emission end face. For example, a mask for shielding light is provided near the light emission end face of the light guide. The mask is, for example, circular, and is aligned with an optical axis Z0 as the center. By providing the mask, the light emitted from the central region in the light emission end face is shielded around the optical axis Z0.

10 Claims, 16 Drawing Sheets

| ANGLE [°] | INCIDENCE (NA=0.56) [%] | COMPARATIVE EXAMPLE 1A (WITH NO MASK) [%] | EXAMPLE 1-1 (WITH A MASK, DIAMETER OF THE MASK :r mm) [%] | COMPARATIVE EXAMPLE 1B (SMALL CORE DIAMETER, CORE DIAMETER :1.35mm) [%] |
|---|---|---|---|---|
| 0.00 | 100.00 | 100.00 | 91.74 | 100.00 |
| 5.00 | 91.84 | 98.16 | 93.73 | 96.98 |
| 10.00 | 70.50 | 95.40 | 99.49 | 91.73 |
| 15.00 | 38.57 | 89.38 | 100.00 | 84.91 |
| 20.00 | 19.10 | 83.61 | 97.86 | 77.87 |
| 25.00 | 8.54 | 76.90 | 92.60 | 67.74 |
| 30.00 | 3.60 | 69.33 | 86.43 | 56.06 |
| 35.00 | 1.57 | 60.53 | 76.93 | 43.67 |
| 40.00 | 0.70 | 49.18 | 63.33 | 31.87 |
| 45.00 | 0.34 | 38.37 | 48.81 | 21.72 |
| 50.00 | 0.20 | 27.26 | 34.73 | 13.87 |
| 55.00 | 0.08 | 18.31 | 23.42 | 8.48 |
| 60.00 | 0.00 | 11.63 | 15.11 | 5.20 |
| 65.00 | 0.00 | 7.18 | 9.16 | 3.19 |
| 70.00 | 0.00 | 4.41 | 5.60 | 1.93 |
| 75.00 | 0.00 | 2.49 | 3.10 | 1.08 |
| 80.00 | 0.00 | 1.15 | 1.41 | 0.49 |
| 85.00 | 0.00 | 0.47 | 0.57 | 0.20 |
| 90.00 | 0.00 | 0.00 | 0.00 | 0.00 |

FIG. 7

| ANGLE [°] | INCIDENCE (NA=0.76) [%] | COMPARATIVE EXAMPLE 1C (WITH NO MASK) [%] | EXAMPLE 1-2 (WITH A MASK, DIAMETER OF THE MASK :0.4mm) [%] | COMPARATIVE EXAMPLE 1D (SMALL CORE DIAMETER, CORE DIAMETER :1.35mm) [%] |
|---|---|---|---|---|
| 0.00 | 100.00 | 100.00 | 100.00 | 100.00 |
| 5.00 | 97.93 | 98.38 | 99.82 | 99.04 |
| 10.00 | 95.86 | 92.92 | 97.62 | 92.97 |
| 15.00 | 86.09 | 90.22 | 94.11 | 88.58 |
| 20.00 | 76.96 | 86.52 | 89.54 | 82.37 |
| 25.00 | 64.35 | 81.79 | 84.08 | 75.28 |
| 30.00 | 49.39 | 74.26 | 77.42 | 66.41 |
| 35.00 | 35.05 | 65.99 | 69.62 | 57.37 |
| 40.00 | 20.00 | 57.24 | 60.22 | 47.83 |
| 45.00 | 7.02 | 48.27 | 51.34 | 38.99 |
| 50.00 | 2.07 | 39.72 | 41.76 | 30.87 |
| 55.00 | 0.63 | 31.63 | 33.36 | 23.97 |
| 60.00 | 0.25 | 24.21 | 25.73 | 18.25 |
| 65.00 | 0.13 | 18.06 | 19.65 | 13.47 |
| 70.00 | 0.80 | 13.21 | 14.50 | 9.62 |
| 75.00 | 0.40 | 8.53 | 9.56 | 6.05 |
| 80.00 | 0.00 | 4.32 | 4.76 | 2.92 |
| 85.00 | 0.00 | 1.81 | 2.09 | 1.28 |
| 90.00 | 0.00 | 0.00 | 0.00 | 0.00 |

FIG. 9

| EXAMPLE 2 (CORE DIAMETER $\phi$=1.55) ||||
|---|---|---|---|
| Si (SURFACE NUMBER) | Ri (RADIUS OF CURVATURE) | Di (SURFACE SEPARATION) | Ni (REFRACTIVE INDEX) |
| 1 | 0 | 2.4 | 1.6 (CORE) 1.52 (CLADDING) |
| 2 | -1.426 | 0.1 | |
| 3 | 0 | 0.6 | 1.883 |
| 4 | -1.538 | 0.1 | |
| 5 | 1.538 | 1.5 | 1.883 |
| 6 | 0 | | |

FIG. 12

| ANGLE [°] | INCIDENCE (NA=0.56) [%] | COMPARATIVE EXAMPLE 2A (WITH NO MASK) [%] | EXAMPLE 2-1 (WITH A MASK, DIAMETER OF THE MASK : 0.4mm) [%] | COMPARATIVE EXAMPLE 2B (SMALL CORE DIAMETER, CORE DIAMETER : 1.35mm) [%] |
|---|---|---|---|---|
| 0.00 | 100.00 | 100.00 | 75.13 | 95.11 |
| 5.00 | 91.84 | 97.49 | 74.61 | 95.40 |
| 10.00 | 70.50 | 90.90 | 82.93 | 100.00 |
| 15.00 | 38.57 | 90.03 | 87.60 | 96.73 |
| 20.00 | 19.10 | 90.60 | 94.42 | 92.90 |
| 25.00 | 8.54 | 86.95 | 98.31 | 87.91 |
| 30.00 | 3.60 | 83.48 | 100.00 | 82.03 |
| 35.00 | 1.57 | 80.01 | 98.83 | 74.60 |
| 40.00 | 0.70 | 75.57 | 97.01 | 66.85 |
| 45.00 | 0.34 | 70.90 | 92.47 | 59.89 |
| 50.00 | 0.20 | 64.64 | 86.18 | 51.15 |
| 55.00 | 0.08 | 57.88 | 76.41 | 40.75 |
| 60.00 | 0.00 | 48.79 | 64.23 | 30.38 |
| 65.00 | 0.00 | 38.94 | 50.37 | 20.45 |
| 70.00 | 0.00 | 27.75 | 35.83 | 12.56 |
| 75.00 | 0.00 | 16.20 | 21.58 | 6.47 |
| 80.00 | 0.00 | 6.72 | 9.60 | 2.78 |
| 85.00 | 0.00 | 2.03 | 3.58 | 1.10 |
| 90.00 | 0.00 | 0.00 | 0.00 | 0.00 |

FIG. 13

| ANGLE [°] | INCIDENCE (NA=0.76) [%] | COMPARATIVE EXAMPLE 2C (WITH NO MASK) [%] | EXAMPLE 2-2 (WITH A MASK, DIAMETER OF THE MASK :0.4mm) [%] | COMPARATIVE EXAMPLE 2D (SMALL CORE DIAMETER, CORE DIAMETER :1.35mm) [%] |
|---|---|---|---|---|
| 0.00 | 100.00 | 89.31 | 94.23 | 100.00 |
| 5.00 | 97.93 | 90.68 | 93.50 | 99.73 |
| 10.00 | 95.86 | 94.73 | 93.62 | 98.18 |
| 15.00 | 86.09 | 96.55 | 94.92 | 96.92 |
| 20.00 | 76.96 | 98.00 | 97.74 | 95.66 |
| 25.00 | 64.35 | 98.79 | 98.22 | 95.47 |
| 30.00 | 49.39 | 100.00 | 100.00 | 97.33 |
| 35.00 | 35.05 | 97.27 | 98.95 | 95.70 |
| 40.00 | 20.00 | 90.95 | 94.14 | 88.52 |
| 45.00 | 7.02 | 79.05 | 83.21 | 73.21 |
| 50.00 | 2.07 | 64.99 | 69.69 | 56.09 |
| 55.00 | 0.63 | 50.98 | 55.09 | 39.01 |
| 60.00 | 0.25 | 38.10 | 41.55 | 25.01 |
| 65.00 | 0.13 | 26.68 | 28.68 | 14.55 |
| 70.00 | 0.80 | 16.42 | 17.89 | 8.42 |
| 75.00 | 0.40 | 8.28 | 9.11 | 4.32 |
| 80.00 | 0.00 | 3.13 | 3.54 | 1.80 |
| 85.00 | 0.00 | 0.96 | 1.16 | 0.69 |
| 90.00 | 0.00 | 0.00 | 0.00 | 0.00 |

FIG. 15

LIGHT GUIDE AND ENDOSCOPE

BACKGROUND OF THE INVENTION

1. Field of the Invention

The present invention relates to a light guide used for guiding illumination light and an endoscope for illuminating an object under observation by the illumination light guided by the light guide and observing the object.

2. Description of the Related Art

There are two types of endoscope, that is, for medical use in observing inside of the body cavity of a patient and for industrial use in observing a water pipe or the like. It is generally dark in the body cavity or the like to be observed by the endoscope, so illumination from an external source is required for the observation. As illumination means of the endoscope, a light guide is typically used. The light guide is composed of a large number of optical fibers tied in a bundle. In the light guide, illumination light incident from an end (incident end) of the light guide is emitted from the other end (light emission end).

Conventionally, various actions have been attempted in order to improve an illumination state in the endoscope. A main action is to make the light distribution of illumination as even as possible in a range from a central region in a field of view to a peripheral region. In general, the illumination using the light guide tends to be too bright in the central region in the field of view in comparison with the peripheral region. Therefore, various proposals for improving an illumination optical system provided at the light emission end of the light guide have been conventionally made. By the effects of the conventional proposals, the light distribution has become even, but the light distribution may be required to become evener.

SUMMARY OF THE INVENTION

The present invention has been achieved to overcome the above problem. It is an object of the present invention to provide a light guide and an endoscope capable of making a light distribution even.

In a light guide according to the invention, an amount of light emitted from a central region in a light emission end face is relatively small in comparison with an amount of light emitted from a peripheral region. More specifically, in the light guide according to the invention, a light shielding member for partially or completely shielding light emitted from the central region in the light emission end face is provided, for example, near the light emission end face. Further, in the light guide according to the invention, optical fibers are aligned, more loosely in the central region in the light emission end face, and more densely in the peripheral region in the light emission end face.

An endoscope according to the invention comprises illumination means for illuminating an object under observation and comprises observation means for observing the object illuminated by the illumination means, wherein the illumination means includes a light guide and an illumination optical system provided at a light emission end face of the light guide, which is configured according to the above-described invention.

In the light guide according to the invention, an amount of light emitted from the central region in the light emission end face is relatively small in comparison with an amount of light emitted from the peripheral region in the light emission end face, so the amount of light in the central region in which it conventionally tended to be brighter is reduced, thereby the light distribution becomes even as a whole.

In the endoscope according to the invention, by illumination with the light distribution made even by the light guide of the invention, an easy-to-observe environment can be obtained.

Other and further objects, features and advantages of the invention will appear more fully from the following description.

BRIEF DESCRIPTION OF THE DRAWINGS

FIG. 7 is a table explaining light distribution characteristics obtained by using the illumination optical system with the configuration shown in FIG. 6, where NA of the light guide is 0.56.

FIG. 9 is a table explaining light distribution characteristics obtained by using the illumination optical system with the configuration shown in FIG. 6, where NA of the light guide is 0.76.

FIG. 12 is a table explaining the configuration of the illumination optical system shown in FIG. 11 with specific numeric values.

FIG. 13 is a table explaining light distribution characteristics obtained by using the illumination optical system with the configuration shown in FIG. 11, where NA of the light guide is 0.56.

FIG. 15 is a table explaining light distribution characteristics obtained by using the illumination optical system with the configuration shown in FIG. 11, where NA of the light guide is 0.76.

DETAILED DESCRIPTION OF THE PREFERRED EMBODIMENTS

Embodiments of the present invention will be described below in detail with accompanying drawings.

Figure 1:
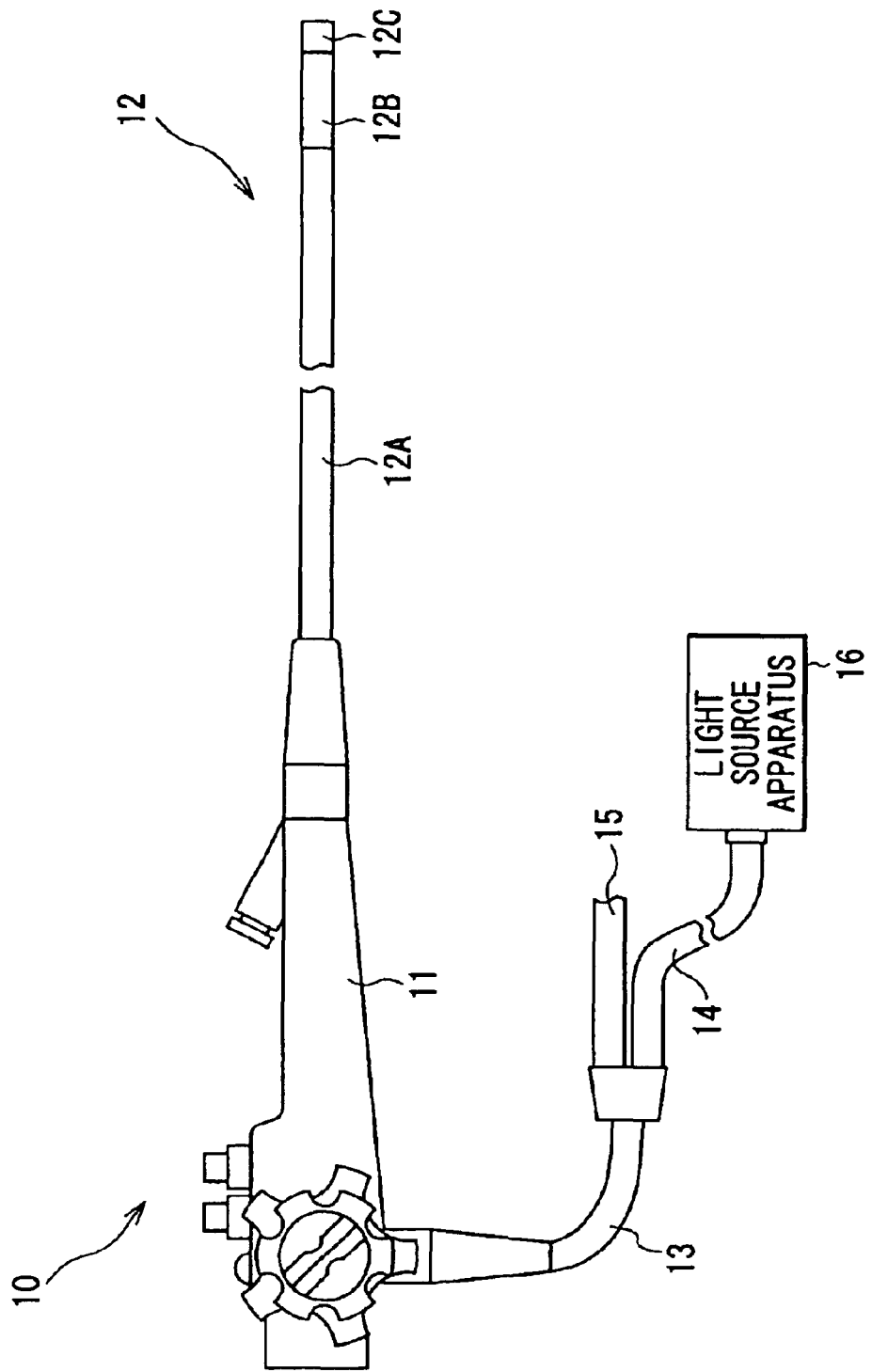
FIG. 1 is an overview showing a configuration of an endoscope according to an embodiment of the present invention.

FIG. 1 shows an overview showing a configuration of an endoscope according to an embodiment of the invention. An endoscope 10 comprises a hand control section 11 which is controlled by an operator, and an insertion section 12 which is connected to an end of the hand control section 11, and is inserted into an object under observation. The insertion section 12 includes a flexible portion 12A, an angle portion 12B and a hard tip portion 12C in order from the side of the hand control section 12. The angle portion 12B is for aiming the hard tip portion 12C at a desired direction, and can be curved by the operation of the hand control section 11.

The endoscope 10 further comprises a flexible cable 13, which is connected to the other end of the hand control section 11. A cable 14 for optical transmission and a cable 15 for image transmission are inserted through the flexible cable 13.

A light guide LG (refer to FIG. 3) comprising a bundle of a large number of optical fibers 41 is inserted through the cable 14. An end (light incident end) of the light guide LG is connected to a light source apparatus 16, while the other end (light emission end) is extended to the hard tip portion 12C. The light source apparatus 16 includes a lamp as a light source, and a condensing lens for condensing light from the lamp into the incident end of the light guide LG, although they are not shown in the drawing. When, like a so-called electronic endoscope (video endoscope), an observation system using a CCD (charge-coupled device) or the like electronically carries out the image transmission, the cable 15 for image transmission includes an electrical signal line. In this case, an end of the signal line included in the cable 15 is connected to an signal processing circuit (not shown), and an signal-processed image is outputted to a monitor or the like (not shown). In the case where the image transmission is optically carried out, like an optical endoscope, the cable 15 for image transmission includes an image guide comprising a bundle of a large number of optical fibers. In this case, an end of the image guide is optically connected to an ocular optical system (not shown), and an optical image transmitted by the image guide is outputted via the ocular optical system. The other end of the signal line or the image guide is extended to the hard tip portion 12C.

Figure 2:
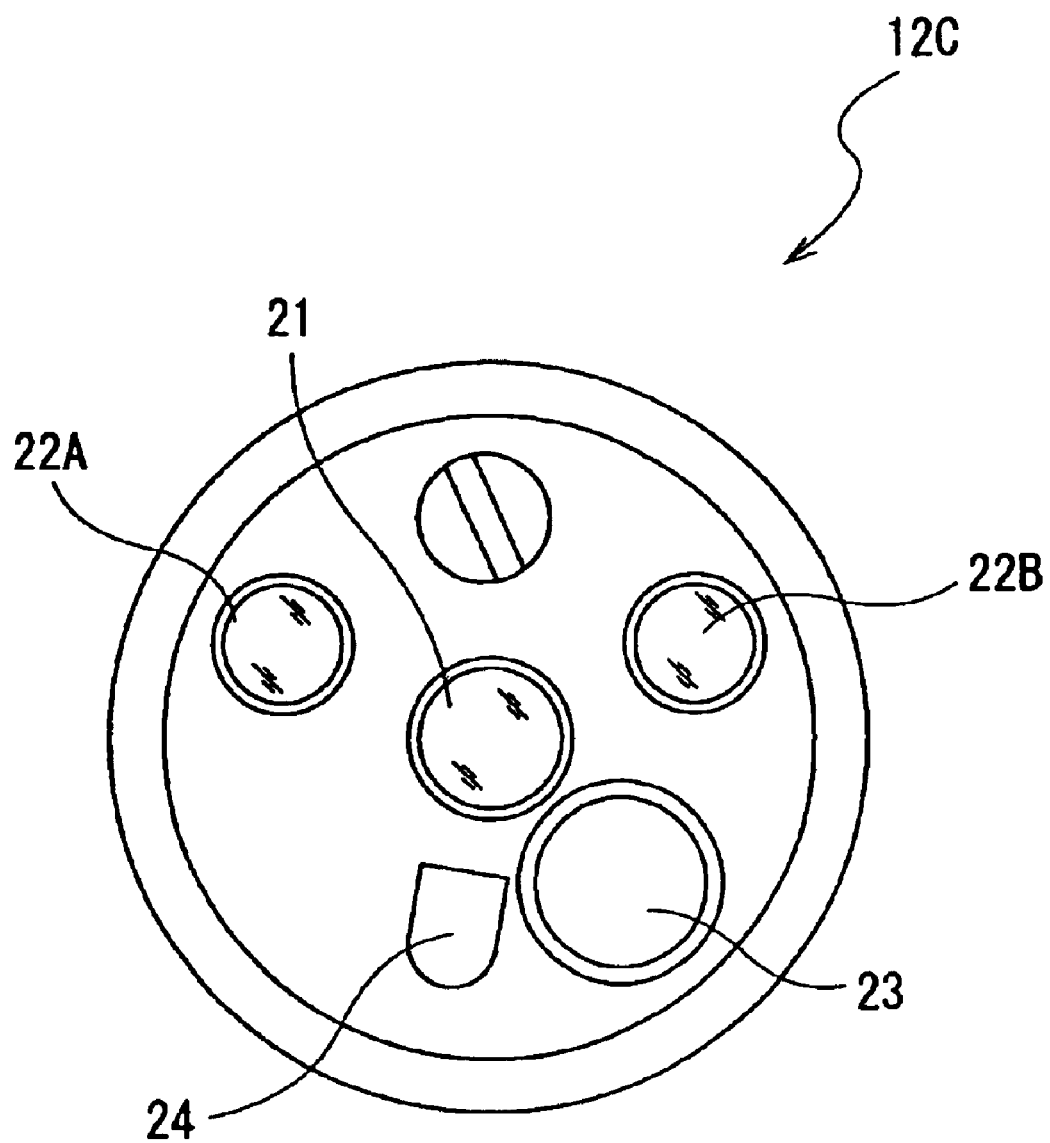
FIG. 2 is an external view showing a configuration of a tip portion of an insertion section in the endoscope shown in FIG. 1.

FIG. 2 shows the configuration of a tip surface of the hard tip portion 12C. At a tip of the hard tip portion 12C, an observation window 21, a pair of illumination windows 22 (22A, 22B), an instrument channel 23 and a nozzle 24 are provided. The instrument channel 23 is for passing an instrument such as clamp or the like therethrough. The nozzle 24 is for providing a liquid for cleaning to the observation window 21.

The observation window 21 is placed, for example, at the center of the tip surface of the hard tip portion 12C. The observation window 21 is for observing an object under observation, and an objective optical system for observation is equipped in the observation window 21. At an image formation side of the objective optical system, an image pickup device such as CCD, an image guide or the like is provided. In the embodiment, a configuration from the observation window 21 to the cable 15 for image transmission via the objective optical system corresponds to a specific example of "observation means" in the invention.

The pair of the illumination windows 22 are placed, for example, at almost the same distance from the observation window 21. Further, the number of the illumination window is not limited to two, but may be only one or more than two. The illumination window 22 is for illuminating the object under observation, and an illumination optical system 30 as shown in FIG. 30 is equipped in the illumination window 22.

Figure 3:
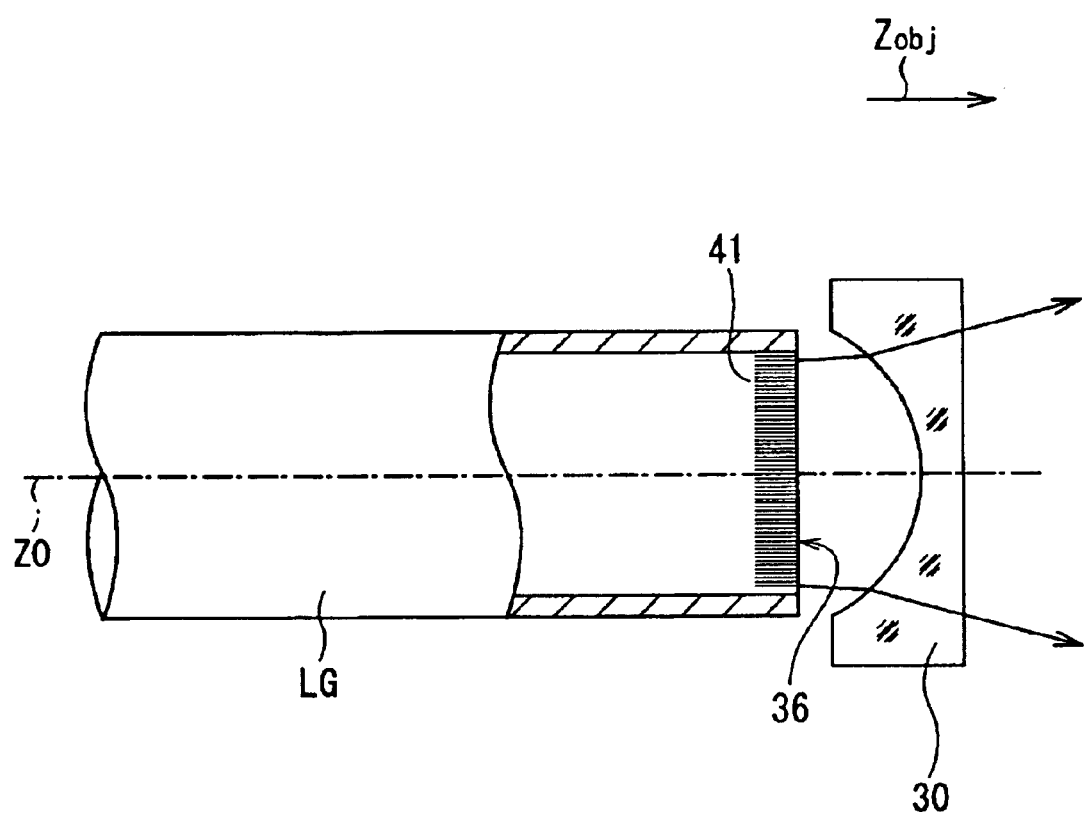
FIG. 3 is a partial cutaway view of a light guide and its illumination optical system according to the embodiment of the invention.

FIG. 3 shows the configuration of a light emission end side of the light guide LG. In FIG. 3, the side indicated by a symbol Zobj is an object side (the side of the illumination window), that is, the side where the illuminating light is emitted. Near the light emission end face of the light guide LG, the illumination optical system 30 is equipped. The illumination optical system 30 has a function of diverging illumination light guided from the light source 16 by the light guide and extending an illuminating range. The illumination optical system 30 may be composed of either a concave lens as shown in FIG. 3 or the combination of a plurality of concave lenses like an illumination optical system 30B (shown in FIG. 11) according to an embodiment described below.

In the light guide LG, an amount of light emitted from the central region in a light emission end face 36 thereof is relatively small in comparison with that emitted from the peripheral region in the light emission end face 36.

Figure 4:
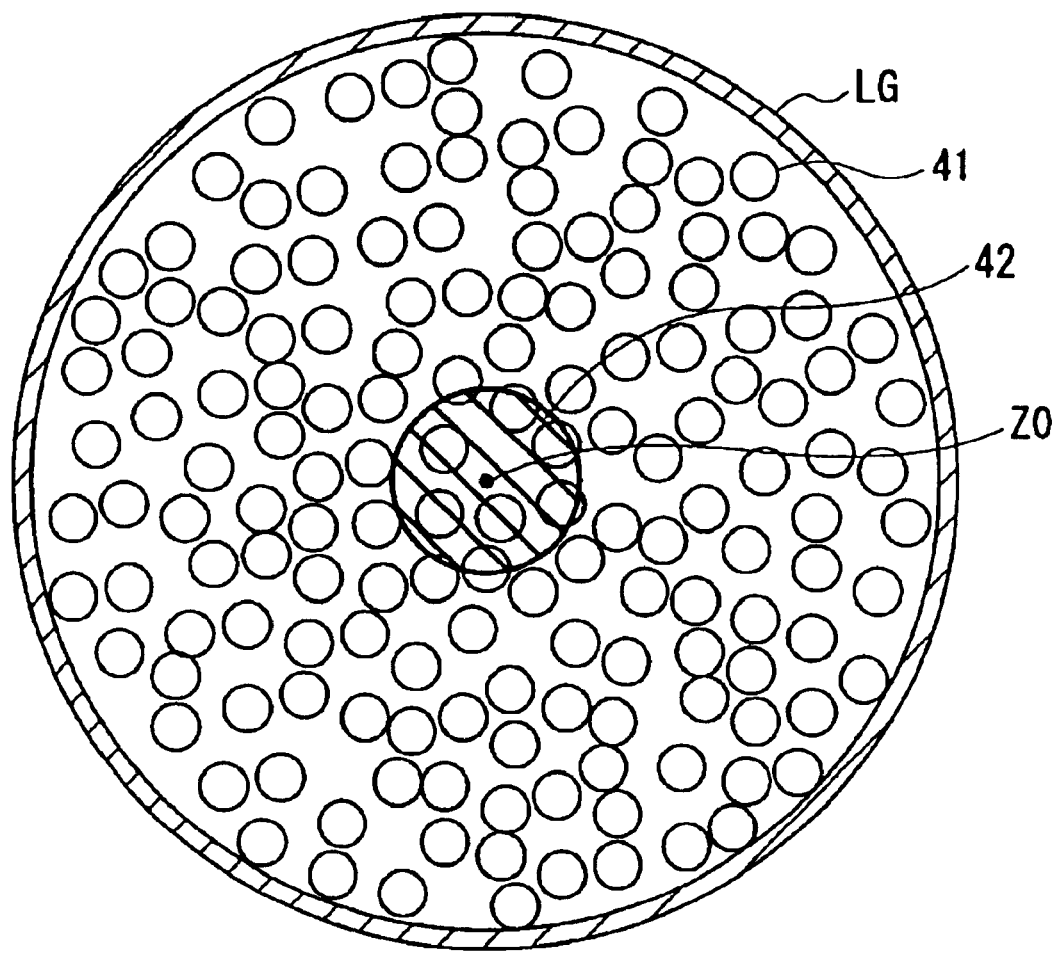
FIG. 4 is an external view showing a configuration example of the light emission end face of the light guide according to the embodiment of the invention.

FIG. 4 shows an example of the configuration of the light emission end face 36 of the light guide LG. The example shown in FIG. 4 has a mask 42 for shielding light, which is placed near the light emission end of the light guide LG. The mask 42 is, for example, circular, and is aligned with an optical axis Z0 as its center. However, the shape of the mask 42 is not limited to be circular but may be, for example, polygonal. The mask 42 is directly attached on the light emission end face 36 of the light guide LG with, for example, an adhesive. The mask 42 may be formed, for example, by black-plating a stainless sheet, or by vapor-depositing a material having light shielding properties onto glass. The material of the mask 42 may be formed of anything capable of shielding light and is not specifically limited. By providing the mask 42, light emitted from the central region in the light emission end face 36 is shielded around the optical axis Z0. In the configuration shown in FIG. 4, only the mask 42 is attached, so the conventional light guide can be used, and the configuration is simple.

Further, in the case where protection glass is provided to protect the end face on the light emission end face 36 of the light guide LG, by vapor-depositing a material having light shielding properties onto the central region in the protection glass, the protection glass can have the same function as the mask 42.

Moreover, the mask 42 may be configured so as to completely or partially shield light. For example, the mask 42 may be configured so that the transparency of the mask 42 increases gradually from the center to its periphery, so the degree of light shielding decreases gradually from the center to its periphery. Such a configuration can be implemented, for example, by forming the mask 42 by vapor-depositing a material having light shielding properties onto glass or the like, thereby having different transparencies between the center and its periphery.

Figure 5:
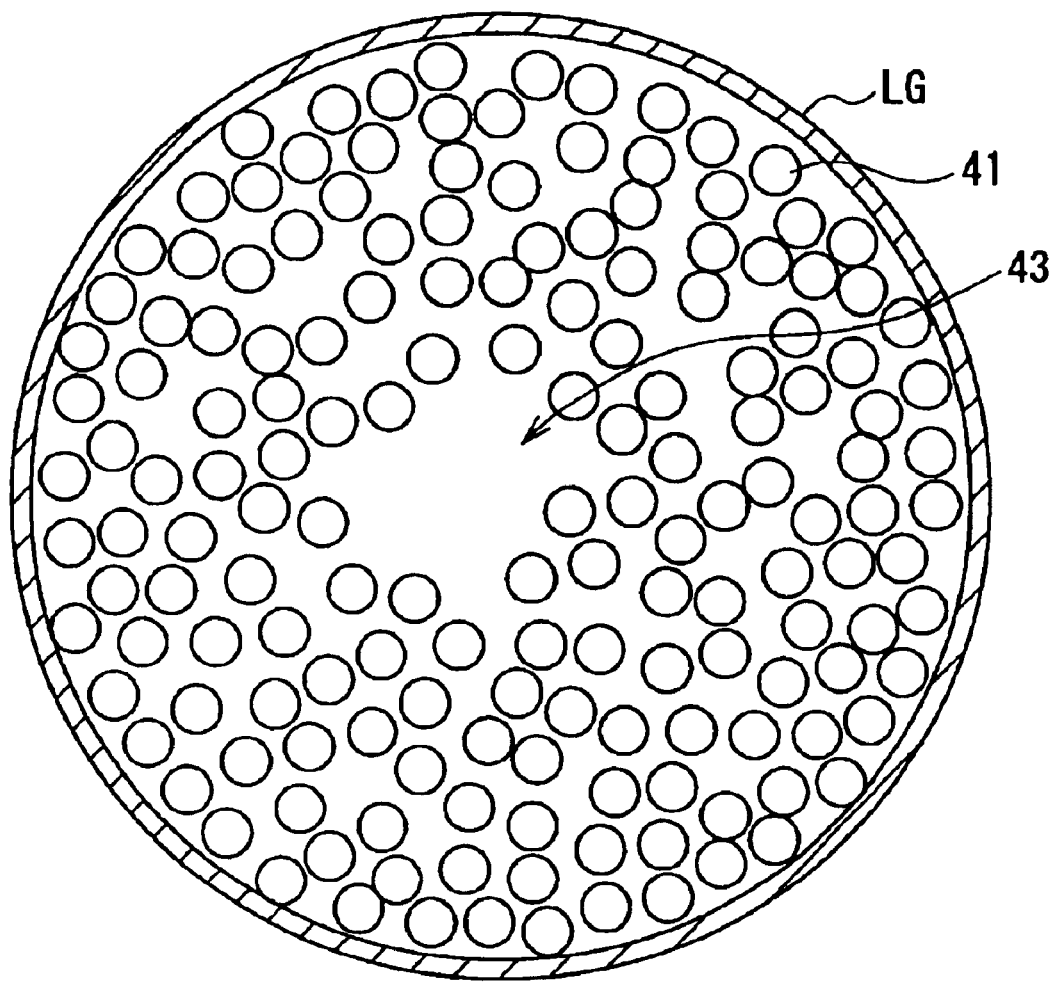
FIG. 5 is an external view showing another configuration example of the light emission end of the light guide according to the embodiment of the invention.

FIG. 5 is another example of the configuration of the light guide LG. In the example of the configuration shown in FIG. 5, the optical fibers 41 included in the light guide LG are aligned, loosely in the central region 43 in the light emission end face, and densely in the peripheral region in the light emission end face. As a method of putting the optical fibers 41 into such an alignment, there is a method of driving a needle-shaped component into the central region 43 in the light emission end like a wedge. In the configuration with the mask 42 provided shown in FIG. 4, as light emitted from the central region is shielded, the loss of the amount of light occurs. On the other hand, in the configuration shown in FIG. 5, all light emitted from the optical fibers 41 can be used, so there is an advantage that no loss of the amount of light occurs.

In the endoscope having the above-described configuration, the amount of light emitted from the central region in the light emission end of the light guide LG is relatively small in comparison with the amount of light emitted from the peripheral region in the light guide LG. Thereby, the amount of light emitted from the central region in which it conventionally tended to be brighter will be reduced. Then, the light emitted from the light guide LG enters into the illumination optical system 30 to be diverged. The divergence of a ray emitted from the illumination optical system 30 is larger than the divergence of a ray emitted from the light emission end face 36 of the light guide LG. Further, by passing the light through the illumination optical system 30, the light distribution of the ray becomes even. In the embodiment, in the light emission end of the light guide LG, a relatively small amount of light is emitted from the central region, so the light distribution after passing through the illumination optical system 30 becomes evener in a range from the central region in a field of view to the peripheral region in comparison with the conventional light distribution. Thus, the light diverged by the illumination optical system 30, of which the light distribution becomes even, illuminates the object under observation via the illumination windows 22 (shown in FIG. 2) as illumination light. The illuminated object is observed from the observation window 21 in the hard tip portion 12C.

EXAMPLE

Next, specific numerical examples of the light distribution obtained by the light guide LG according to the embodiment will be described below. In the examples, it is assumed that the light guide LG is used for an endoscope with a viewing angle of 140 degrees.

Example 1

Figure 6:
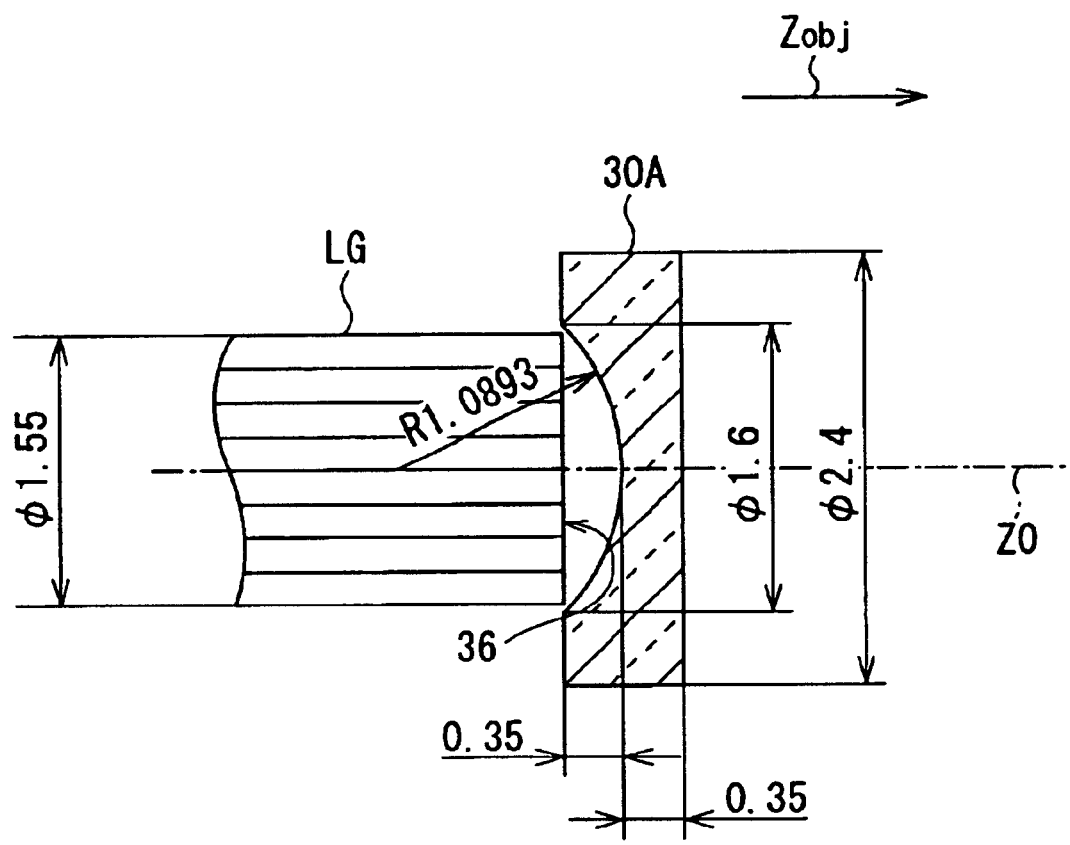
FIG. 6 is a cross section showing the configuration of an illumination optical system used in a first specific numerical example (Example 1) of the light distribution obtained by the light guide according to the embodiment of the invention.

As a first example, as shown in FIG. 6, an example using the illumination optical system 30A composed of a concave lens facing its concave surface toward the light emission end of the light guide is shown. The diameter of the concave lens and the radium of curvature of the concave surface are as shown in the drawing. All dimensions are in millimeters. The refractive index Nd relative to the d-line (wavelength $\lambda_d$=587.6 nm) of glass forming the concave lens is 1.883. The core diameter of the light guide LG is 1.55 mm.

Figure 8:
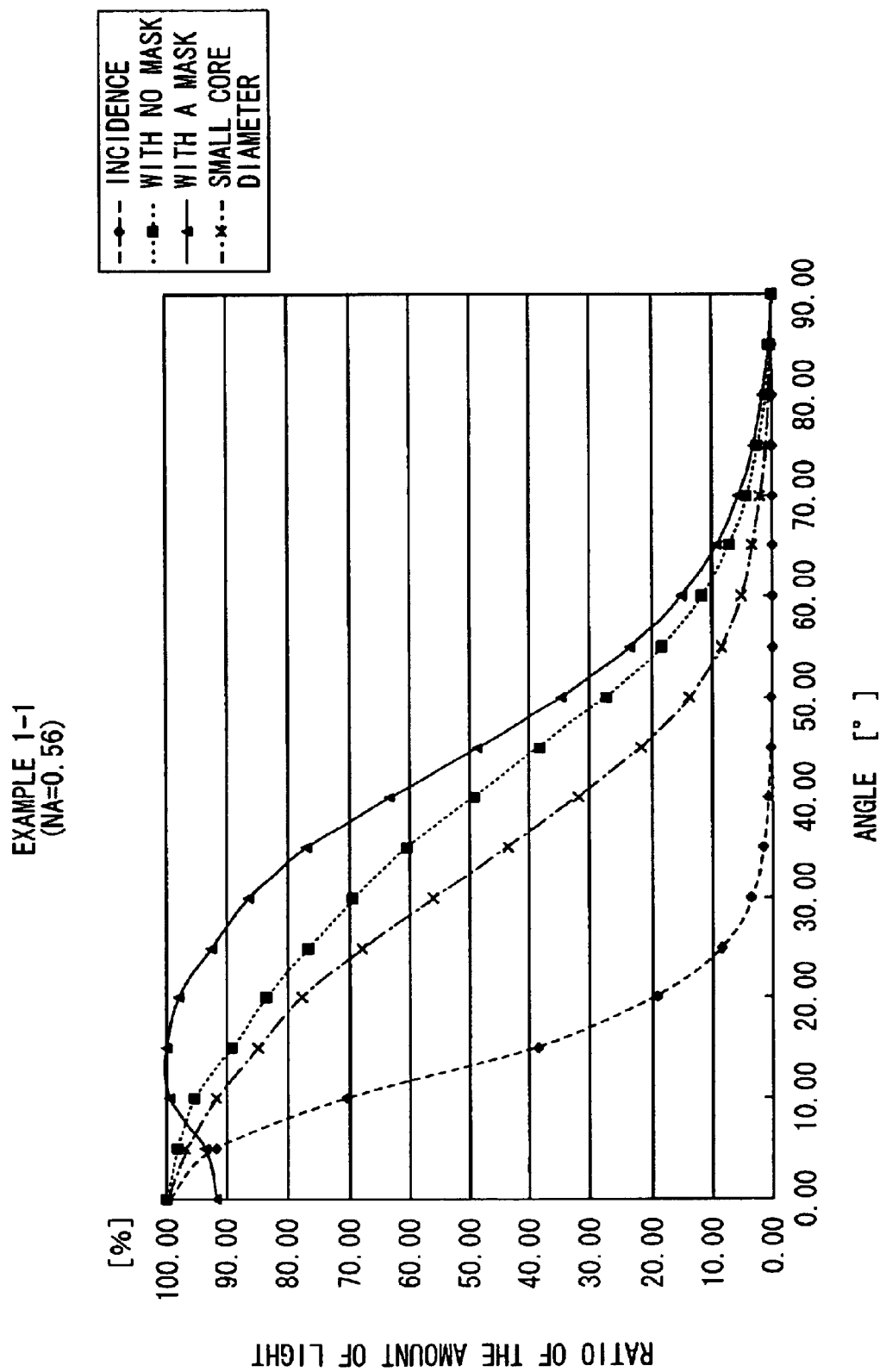
FIG. 8 is a graphic plot of the light distribution characteristics shown in FIG. 7.

FIG. 7 numerically shows the light distribution characteristics (light distribution) of the illumination optical system with the configuration shown in FIG. 6. In FIG. 8, values indicating the light distribution characteristics shown in FIG. 7 are plotted in a graph with the horizontal axis indicating angle and the vertical axis indicating ratio of the amount of light. In FIG. 7, in the illumination optical system with the configuration shown in FIG. 6, the light distribution characteristics in the case where a mask with a diameter of 0.4 mm is provided on the light emission end face 36 of the light guide LG are shown in the column of "Example 1-1". In FIG. 7 and FIG. 8, the light distribution characteristics of comparative examples relative to Example 1-1 are also shown. As the comparative examples, in the illumination optical system with the configuration shown in FIG. 6, there are two comparative examples in the case where no mask is provided on the light emission end of the light guide LG (comparative example 1A) and in the case where the core diameter of the light guide is smaller (comparative example 1B). In the comparative example 1B, contrary to the example, it is assumed that a mask is provided on the periphery of the light guide LG to shield light in the periphery, and the core diameter of the light guide LG is 1.35 mm.

In FIG. 7, "angle" indicates an angle relative to the optical axis Z0. The values in the column of "incidence" indicate the light distribution of light emitted from the light emission end face 36 of the light guide LG, that is, the light distribution of light entering into the illumination optical system 30A. The value in the columns of "Example 1-1", "comparative example 1A" and "comparative example 1B" indicate the light distribution in the state after the light, which has entered from the light emission end face 36 of the light guide LG into the illumination optical system 30A in the state of the light distribution shown in the column of "incidence", passes through the illumination optical system 30A. In each column, the value indicating the light distribution is a ratio of the amount of light at each angle, assuming that the amount of light at an angle at which the maximum amount of light is achieved is 100.

FIG. 7 shows an example that the angle of the light distribution from the light guide LG is relatively narrow. More specifically, it is assumed that the refractive index of each medium forming the core and the cladding of the light guide LG is 1.62 and 1.52, respectively, and the numerical aperture is NA=0.56 ($\theta$=34 degrees).

The light distribution of the light source at the side of the incident end has a large influence upon the light distribution from the light emission end of the light guide LG. However, NA of the light guide LG is determined by the refractive indexes of media forming the core and the cladding of the light guide LG. That is, assuming that the refractive index of each medium forming the core and the cladding of the light guide LG is $n_1$ and $n_2$, respectively, NA is given by the following formula:

$$NA=(N_1^2-n_2^2)^{1/2}=\sin\theta.$$

$\theta$ is the incident angle of illumination light into the light guide LG.

Figure 10:
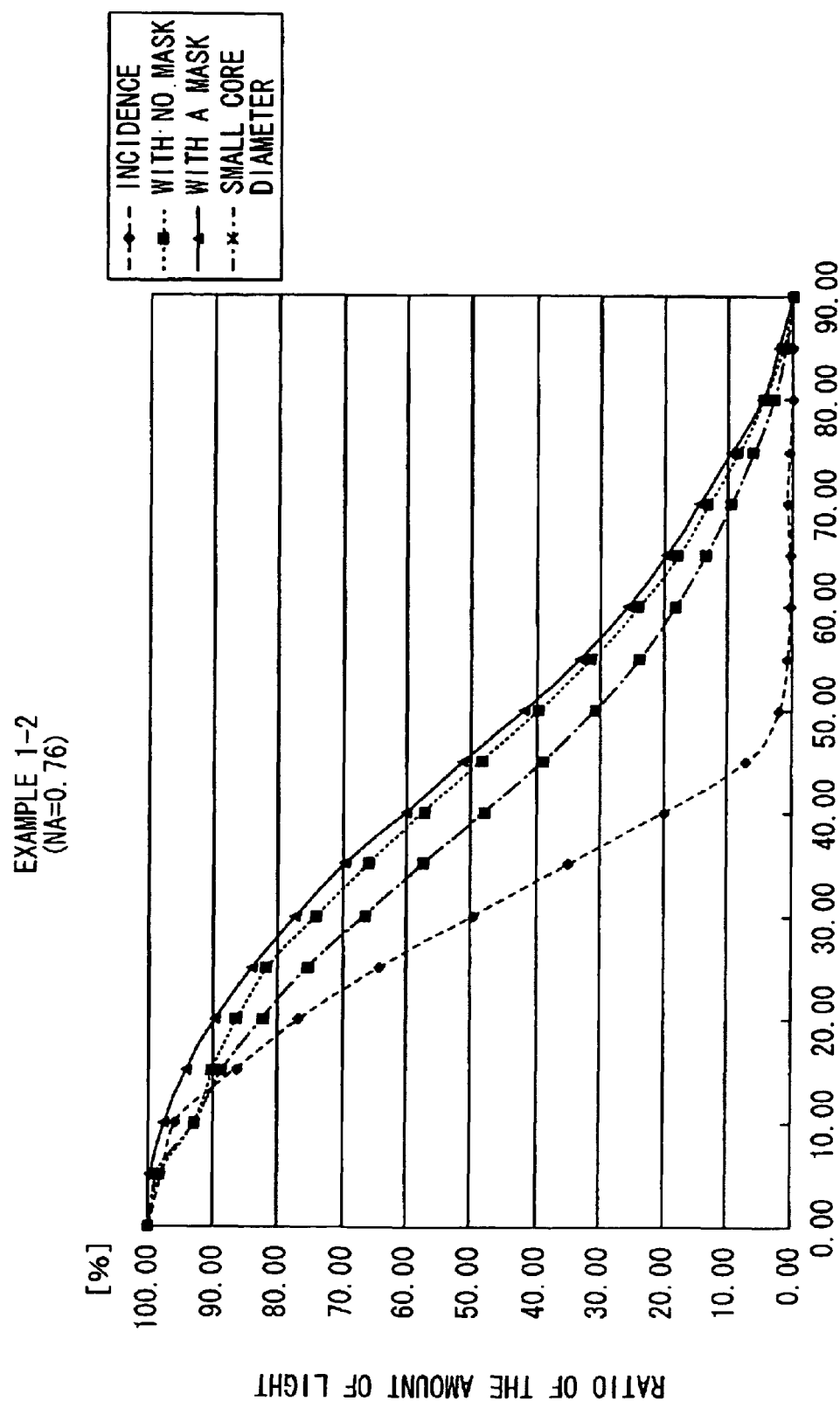
FIG. 10 is a graphic plot of the light distribution characteristics shown in FIG. 9.

On the other hand, an example that the angle of the light distribution from the light guide LG is relatively wide is shown in FIG. 9 and FIG. 10. Like FIG. 7, FIG. 9 numerically shows the light distribution characteristics (light distribution). In FIG. 10, values indicating the light distribution characteristics shown in FIG. 9 are plotted in a graph with the horizontal axis indicating angle and the vertical axis indicating ratio of the amount of light. The indication of each value shown in FIG. 9 is the same as that in FIG. 7.

In FIG. 9, it is assumed that the refractive index of each medium forming the core and the cladding of the light guide LG is 1.66 and 1.48, respectively, and the numerical aperture is NA=0.76 ($\theta$=50 degrees). In FIG. 9, like the example in FIG. 7, in the illumination optical system with the configuration shown in FIG. 6, the light distribution characteristics in the case where a mask with a diameter of 0.4 mm is provided on the light emission end face of the light guide LG are shown in the column of "Example 1-2". In FIG. 9 and FIG. 10, the light distribution characteristics of two comparative examples 1C and 1D relative to Example 1-2 are also shown. The conditions of the comparative examples 1C and 1D are the same as those of the comparative examples in FIG. 7, except that NA is 0.76.

Example 2

Figure 11:
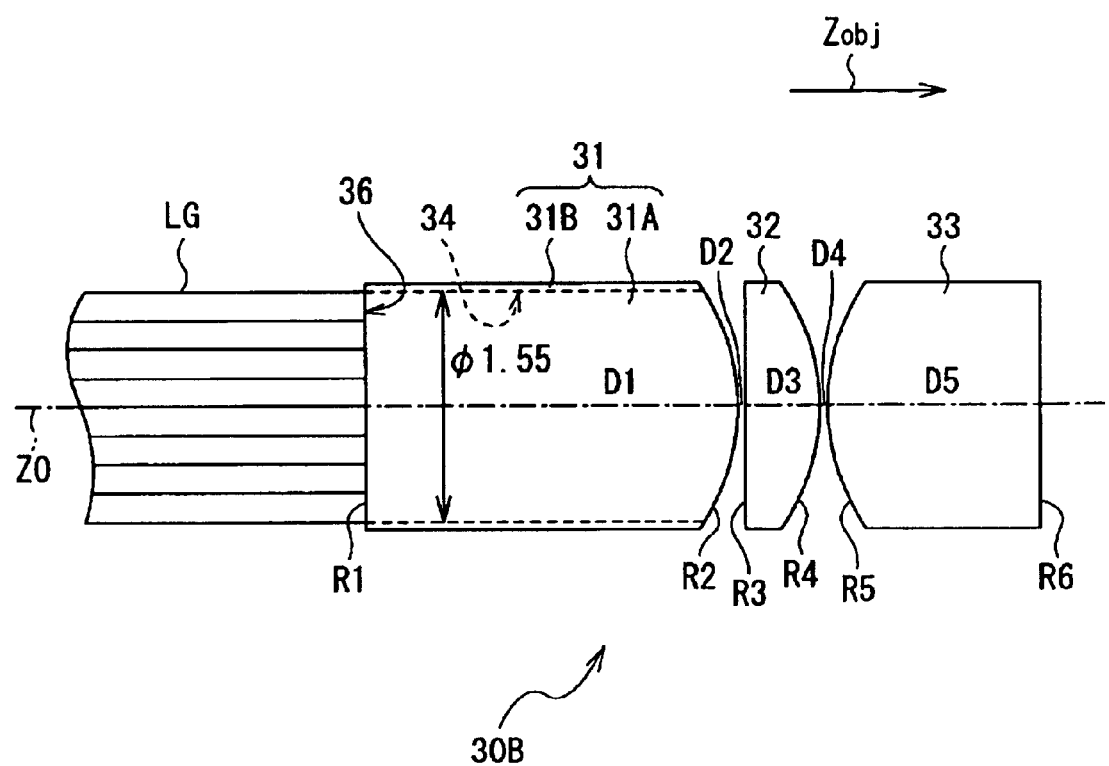
FIG. 11 is a cross section showing the configuration of an illumination optical system used in a second specific numerical example (Example 2) of the light distribution obtained by the light guide according to the embodiment of the invention.

Next, as a second example, as shown in FIG. 11, an example using the illumination optical system 30B composed of a convex lens system provided on the light emission end of the light guide LG will be described.

In FIG. 11, a symbol Ri indicates the radius of curvature of the ith surface from the light emission end face, assuming that the surface nearest the light emission end face (the light emission end face of the light guide LG) is the first surface. A symbol Di indicates the surface separation on the optical axis between the ith surface and i+1th surface.

The illumination optical system 30B used in the example comprises an optical element 31 and two plano-convex lenses 32 and 33 in order from the light emission end face of the light guide LG. Two plano-convex lenses 32 and 33 constitute a two-lens system. The convex surface of the plano-convex lens 32 faces toward the object side, while the convex surface of the plano-convex lens 33 faces toward the light emission end face.

The optical element 31 is rod-lens-shaped, and is configured so that a cladding 31B, which has a lower refractive index than a core 31A that is a component of the central region, is provided around the core 31A. The optical element 31 is plano-convex-shaped as a whole, and the surface at the light guide side (R1) is plane and the surface at the object side is convex. As the surface at the object side in the optical element 31 is convex, the optical element 31 has a function as a convex lens at the light emission side. Also the optical element 31 has a function of totally reflecting the light incident on a range from the light emission end of the light guide LG to its periphery (side surface portion) at a boundary surface 34 between the core 31A and the cladding 31B by the difference in their refractive indexes. Thereby, a ray from the light guide LG can be used as illumination light with no loss.

FIG. 12 shows the configuration of the illumination optical system 30B with specific numeric values. In FIG. 12, a surface number Si indicates the number of a surface from the light emission end face, assuming the surface nearest the light emission end face (the light emission end face of the light guide LG) is the first surface. A refractive index Ndi indicates a value relative to the d-line. A radius of curvature Ri, like the symbol Ri shown in FIG. 11, indicates the radius of curvature of the ith lens surface from the light emission end face. A surface separation Di, like the symbol Di shown in FIG. 11, indicates the surface separation on the optical axis between the ith surface Si from the light emission end face and the i+1th surface Si+1. The radius of curvature Ri and the surface separation Di are expressed in millimeter. Further, in the drawing, the surface with a radius of curvature Ri of 0 is plane. In FIG. 12, the core diameter $\phi$ of the optical element 31 provided nearest the light emission end face of the light guide LG is shown.

Figure 14:
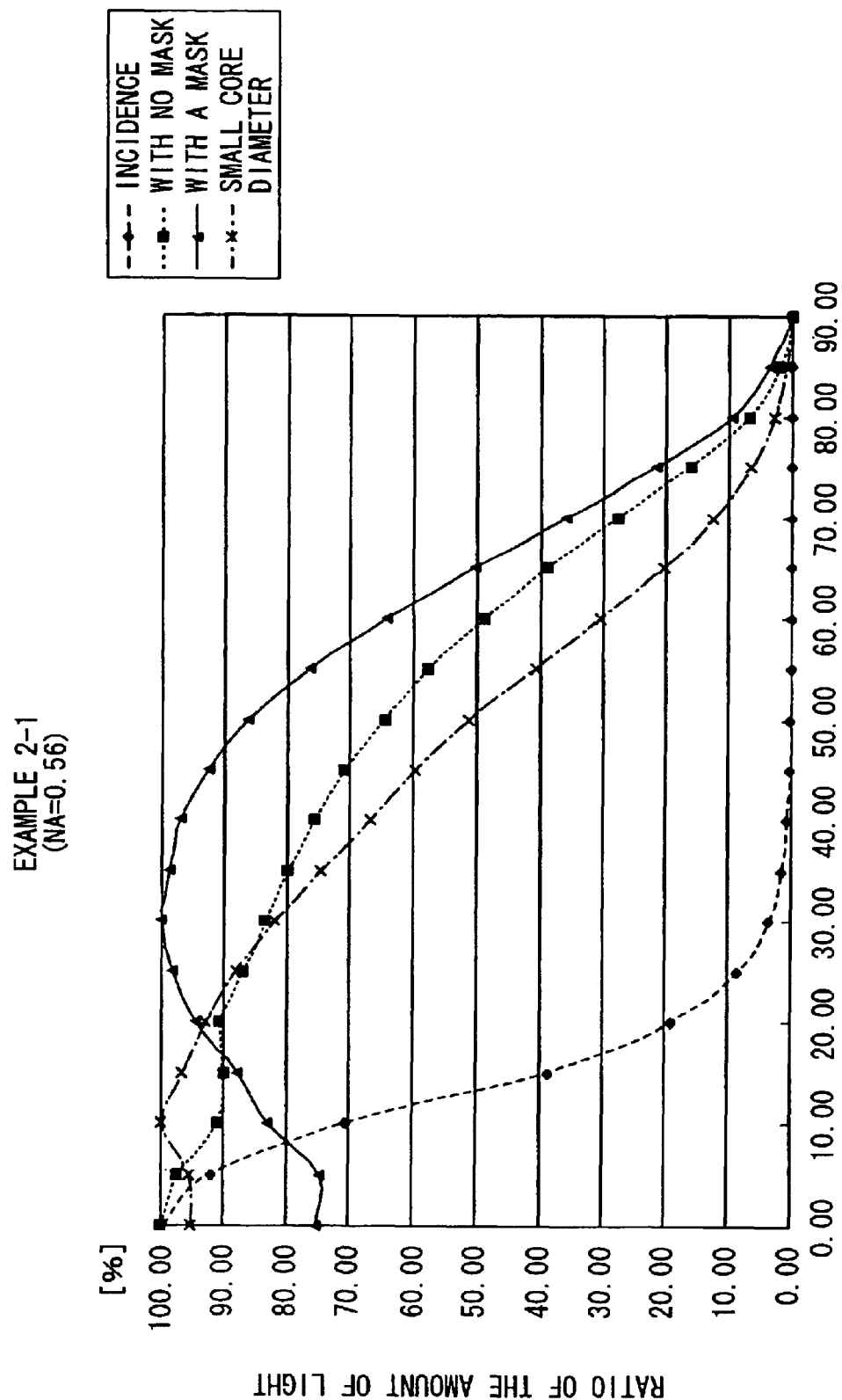
FIG. 14 is a graphic plot of the light distribution characteristics shown in FIG. 13.

FIG. 13 numerically shows the light distribution characteristics (light distribution) of the illumination optical system with the configuration shown in FIG. 11. In FIG. 14, values indicating the light distribution characteristics shown in FIG. 13 are plotted in a graph with the horizontal axis indicating angles and the vertical axis indicating ratio of the amount of light. The indication of each value shown in FIG. 13 is the same as that in FIG. 7.

In FIG. 13, in the illumination optical system with the configuration shown in FIG. 11, the light distribution characteristics in the case where a mask with a diameter of 0.4 mm is provided on the light emission end face 36 of the light guide LG are shown in the column of "Example 2-1". In FIG. 13 and FIG. 14, the light distribution characteristics of comparative examples relative to Example 2-1 are also shown. Like Example 1, as the comparative examples, in the illumination optical system with the configuration shown in FIG. 11, there are two comparative examples in the case where no mask is provided on the light emission end of the light guide LG (comparative example 2A) and in the case where the core diameter of the light guide is smaller (comparative example 2B). In the comparative example 2B, contrary to the example, it is assumed that a mask is provided on the periphery of the light guide LG to shield light in the periphery, and the core diameter of the light guide LG is 1.35 mm.

FIG. 13 shows an example that the angle of the light distribution from the light guide LG is relatively narrow. More specifically, it is assumed that the refractive index of each medium forming the core and the cladding of the light guide LG is 1.62 and 1.52, respectively, and the numerical aperture is NA=0.56 ($\theta$=34 degrees).

Figure 16:
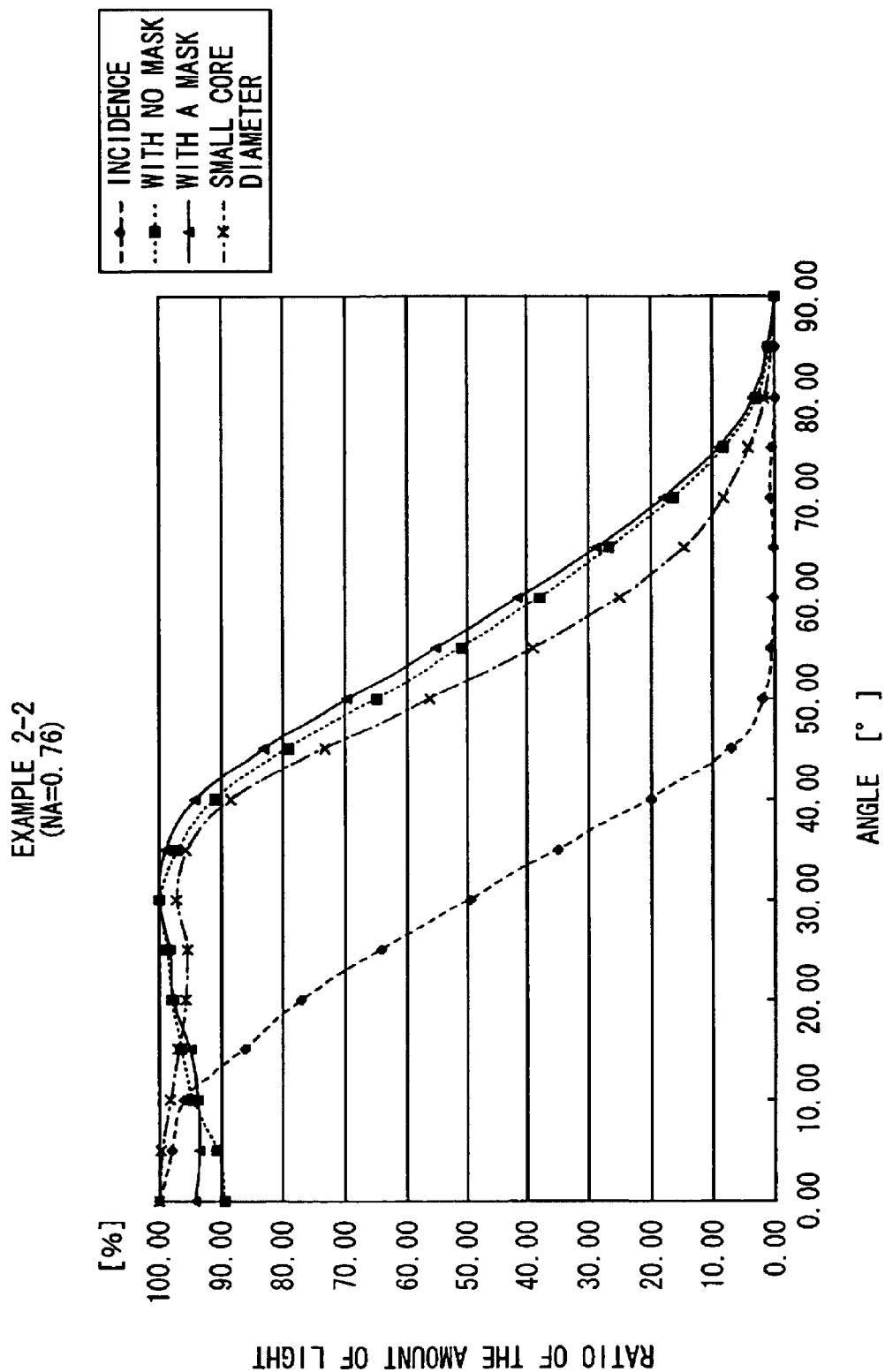
FIG. 16 is a graphic plot of the light distribution characteristics shown in FIG. 15.

On the other hand, in the illumination optical system with the configuration shown in FIG. 11, an example that the angle of the light distribution from the light guide LG is relatively wide is shown in FIG. 15 and FIG. 16. Like FIG. 13, FIG. 15 numerically shows the light distribution characteristics (light distribution). In FIG. 16, values indicating the light distribution characteristics shown in FIG. 15 are plotted in a graph with the horizontal axis indicating angle and the vertical axis indicating ratio of the amount of light. The indication of each value shown in FIG. 15 is the same as that in FIG. 7.

In FIG. 15, it is assumed that the refractive index of each medium forming the core and the cladding of the light guide LG is 1.66 and 1.48, respectively, and the numerical aperture is NA=0.76 ($\theta$=50 degrees). In FIG. 15, like the example in FIG. 13, in the illumination optical system with the configuration shown in FIG. 11, the light distribution characteristics in the case where a mask with a diameter of 0.4 mm is provided on the light emission end face of the light guide LG are shown in the column of "Example 2-2". In FIG. 15 and FIG. 16, the light distribution characteristics of two comparative examples 2C and 2D relative to Example 2-2 are also shown. The conditions of the comparative examples 2C and 2D are the same as those of the comparative examples in FIG. 13, except that NA is 0.76.

As is evident from the above examples, each example with a mask provided at the light emission end face 36 of the light guide LG has an evener light distribution in comparison with each comparative example. Further, from the viewpoint of the light distribution characteristics shown in each drawing, it can be said that a system configured of only a concave lens, which is frequently used as an illumination optical system, conventionally had an advantage of making the light distribution relative to a light guide with large NA uniform, but the optical system using a mask according to the examples has a great effect of making the light distribution relative to a light guide LG with small NA uniform and even (refer to FIG. 8 and FIG. 14). In the light guide LG with large NA, a component with high refractive index is generally used for the core, but the component with high refractive index is easy to be stained, thereby resulting in a decrease in the transparency. Further, in order to increase NA of the light guide LG, it is required to enter a ray with a large incident angle into the incident end of the light guide LG. It leads upsizing of the light source and the optical system for the light source which makes light from the light source enter into the light guide LG. As the optical system according to the examples has a larger effect of making the light distribution relative to the light guide with small NA, it has an advantage in the transparency and the configuration at the light source side, thereby, the cost of the light guide LG and the size of the configuration at the light source side can be reduced.

As described above, in the light guide LG according to the embodiment, an amount of light emitted from the central region in the light emission end face 36 is relatively small in comparison with an amount of light emitted from the peripheral region in the light emission end face 36, so compared with the conventional light guide, the light distribution can become evener.

Further, in the endoscope according to the embodiment, illumination with the light distribution made even by the light guide LG according to the embodiment is provided, so an easy-to-observe environment can be obtained.

The present invention is not limited to the above-described embodiment, but is applicable for various modifications. For example, the light guide according to the invention is not limited to be used for the endoscope but is widely applicable for any apparatus using the light guide.

Any illumination optical system provided on the light emission end of the light guide, other than that with the configurations shown in the examples may be used. Even if an illumination optical system with any other configuration is used, the light guide according to the examples can achieve the effect of making the light distribution even. For example, in FIG. 11, the optical element 31 composed of a single optical component has a function of light reflection and a function as a convex lens, while the functions which the optical element 31 has may be achieved by the combination of an optical component with the function of light reflection and a convex lens. In this case, the function of light reflection by the optical component may be achieved by total reflection using a difference of the refractive index between a core component and a cladding component, or by using specular reflection made by plating the periphery of the optical component. Further, in the illumination optical system 30B shown in FIG. 11, all components are plano-convex, but at least one component may be biconvex.

As described above, in the light guide according to the invention or the endoscope according to the invention, an amount of light emitted from the central region in the light emission end face is relatively small in comparison with an amount of light emitted from the peripheral region in the light emission end face, thereby the light distribution can become even.

Specifically, in the light guide according to an aspect of the invention or the endoscope according to an aspect of the invention, by providing light shielding member for partially or completely shielding light emitted from the central region in the light emission end face, the amount of light emitted from the central region in the light emission end face is reduced, thereby the conventional light guide can be used and the configuration is simple.

More specifically, in the light guide according to another aspect of the invention or the endoscope according to another aspect of the invention, as optical fibers are aligned, more loosely in the central region in the light emission end face, and more densely in the peripheral region in the light emission end face, light emitted from all of the optical fibers can be used, thereby no loss in the amount of light occurs. Therefore, without losing the amount of light, the light distribution can become even.

Obviously many modifications and variations of the present invention are possible in the light of the above teachings. It is therefore to be understood that within the scope of the appended claims the invention may be practiced otherwise than as specifically described.

What is claimed is:

1. A light guide comprising a bundle of a large number of optical fibers, and emitting illumination light guided by the optical fibers from a light emission end face, wherein an amount of light emitted from a central region in the light emission end face is relatively small in comparison with an amount of light emitted from a peripheral region in the light emission end face, wherein a mask for partially or completely shielding light emitted from the central region in the light emission end face is provided near the light emission end face.

2. A light guide according to claim 1, wherein an illumination optical system composed of a plano-concave lens is provided near the light emission end face.

3. A light guide according to claim 1, further comprising an illumination optical system near the light emission end face, the illumination optical system including an optical element and at least one convex lens, the optical element having a side face with a function of light reflection and having a light emission face with a function of a convex lens.

4. A light guide comprising a bundle of a large number of optical fibers, and emitting illumination light guided by the optical fibers from a light emission end face, wherein an amount of light emitted from a central region in the light emission end face is relatively small in comparison with an amount of light emitted from a peripheral region in the light emission end face; and wherein an illumination optical system is provided near the light emission end face, the illumination optical system including an optical element and at least one convex lens, the optical element having a side face with a function of light reflection and having a light emission face with a function of a convex lens.

5. A light guide comprising a bundle of a large number of optical fibers, and emitting illumination light guided by the optical fibers from a light emission end face, wherein an amount of light emitted from a central region in the light emission end face is relatively small in comparison with an amount of light emitted from a peripheral region in the light emission end face, wherein the optical fibers are aligned more loosely in the central region in the light transmission end face, and more densely in the peripheral region in the light emission end face, and wherein an illumination optical system is provided near the light emission end face, the illumination optical system including an optical element and at least one convex lens, the optical element having a side face with a function of light reflection and having a light emission face with a function of a convex lens.

6. An endoscope comprising illumination means for illuminating an object under observation and comprising observation means for observing the object illuminated by the illumination means, the illumination means including:

a light guide having a bundle of a large number of optical fibers, and an illumination optical system provided at a light emission end face of the light guide, wherein an amount of light emitted from a central region in the light emission end face of the light guide is relatively small in comparison with an amount of light emitted from a peripheral region in the light emission end face, wherein a mask for partially or completely shielding light emitted from the central region in the light emission end face is provided near the light emission end face of the light guide.

7. An endoscope according to claim 6, wherein the illumination optical system is composed of a plano-convex lens.

8. An endoscope according to claim 6, wherein the illumination optical system comprising an optical element and at least one convex lens provided in order from the light emission end face, the optical element having a side face with a function of light reflection and having a light emission face with a function of a convex lens.

9. An endoscope comprising illumination means for illuminating an object under observation and comprising observation means for observing the object illuminated by the illumination means, the illumination means including:

a light guide having a bundle of a large number of optical fibers, and an illumination optical system provided at a light emission end face of the light guide, wherein an amount of light emitted from a central region in the light emission end face of the light guide is relatively small in comparison with an amount of light emitted from a peripheral region in the light emission end face; and wherein the illumination optical system includes an optical element and at least one convex lens provided in order from the light emission end face, the optical element having a side face with a function of light reflection and having a light emission face with a function of a convex lens.

10. An endoscope comprising illumination means for illuminating an object under observation and comprising observation means for observing the object illuminated by the illumination means, the illumination means including:

a light guide having a bundle of a large number of optical fibers, and an illumination optical system provided at a light emission end face of the light guide, wherein an amount of light emitted from a central region in the light emission end face of the light guide is relatively small in comparison with an amount of light emitted from a peripheral region in the light emission end face; and wherein the illumination optical system includes an optical element and at least one convex lens provided in order from the light emission end face, the optical element having a side face with a function of light reflection and having a light emission face with a function of a convex lens; and wherein the optical fibers of the light guide are aligned, more loosely in the central region in the light emission end face, and more densely in the peripheral region in the light emission end face.

* * * * *